ically, the ketone which is to be dehydrated to produce the ethynylbenzene according to this invention can be expressed by the following formula:

United States Patent [19]
Amirnazmi

[11] 4,120,909
[45] Oct. 17, 1978

[54] PREPARATION OF ETHYNYLBENZENES

[75] Inventor: Ali Amirnazmi, Tehran, Iran

[73] Assignee: Hercules Incorporated, Wilmington, Del.

[21] Appl. No.: 823,882

[22] Filed: Aug. 11, 1977

[51] Int. Cl.$^2$ .............................................. C07C 15/09
[52] U.S. Cl. .......................... 260/668 R; 260/668 D
[58] Field of Search ............... 260/668 R, 668 D, 681

[56] References Cited

U.S. PATENT DOCUMENTS

| | | | |
|---|---|---|---|
| 1,098,859 | 6/1914 | Webel | 260/681 |
| 1,977,178 | 10/1934 | Dohse et al. | 260/668 R |
| 2,443,732 | 6/1948 | Ipatieff | 260/668 R |

*Primary Examiner*—Veronica O'Keefe
*Attorney, Agent, or Firm*—John W. Whitson

[57] ABSTRACT

Ethynylbenzenes are prepared by the vapor phase catalytic dehydration of methyl phenyl ketones. The dehydration process is carried out at temperatures of from about 500° to about 650° C. using an alumina-containing catalyst. An example of the process is the dehydration of acetophenone to form phenylacetylene.

9 Claims, No Drawings

PREPARATION OF ETHYNYLBENZENES

This invention relates to a process of preparing ethynylbenzenes. More particularly, it relates to a process involving the vapor phase catalytic dehydration of methyl phenyl ketones to produce compounds such as phenylacetylene, m-diethynylbenzene and p-diethynylbenzene. The methyl phenyl ketones used in the process are acetylbenzenes in which the benzene ring is unsubstituted except for one or more acetyl groups.

It is known that ethynylbenzenes may be produced by means of halogenation and dehydrohalogenation reactions. For example, phenylacetylene may be prepared by the addition of bromine to styrene to produce α,β-dibromoethylbenzene and then removing two molecules of hydrogen bromide from the dibromo compound by treatment with an alkali. A modification of this procedure involves preparation of the α,β-dibromoethylbenzene by bromination of ethylbenzene. Following comparable procedures, it is possible to prepare m- or p-diethynylbenzene using the corresponding divinylbenzene or diethylbenzene as the starting material. However, these halogenation-dehydrohalogenation processes generally are characterized by being expensive and complicated and by giving comparatively low yields of the desired products.

Now in accordance with this invention, it has been found that methyl phenyl ketones may be catalytically dehydrated in the vapor phase by bringing them into contact with an alumina-containing catalyst at a temperature in the range of from about 500° to about 650° C., thereby producing ethynylbenzenes as the principal reaction products. By proper control of reaction conditions, the desired ethynylbenzene products can be obtained at high conversions and with minimum formation of undesirable by-products.

In carrying out the process of this invention, acetophenone, for example, is passed through a preheater operated at a temperature sufficiently high to effect vaporization of the ketone. The ketone vapor then is passed through a tubular reactor containing gamma-alumina, for example, as the catalyst, the temperature of the reactor being in the range of about 500° to about 650° C. The partial pressure of the ketone as it enters the reactor is in the range of about 5 to about 30 mm. of mercury and the contact time for the ketone with the catalyst is in the range of from about 0.01 to about 0.05 second. The gaseous mixture exiting from the reactor then is cooled, usually in two or more stages in order to effect a rough separation of the products of the reaction. Further separation of the reaction products may be effected by fractional distillation.

Having generally outlined the embodiments of this invention, the following examples constitute specific illustrations thereof. In these examples, the total fractional conversion, $f$, at the exit of the flow reactor is defined by the following equation:

$$f = 1 - (n'/n)$$

where $n'$ is the total number of moles of ketone collected in the product stream for a certain time on stream and $n$ is the total number of moles of ketone fed into the reactor during the same period of time. The selectivity, $S$, for ethynylbenzene formation at the exit of the reactor is defined as:

$$S = f'/f$$

where $f'$ is the fractional conversion of the ketone to the ethynylbenzene and $f$ is the total fractional conversion. The contact time, $t$, in the flow reactor is obtained from the equation:

$$t = V'/V$$

where $V'$, in cubic centimeters, is the apparent catalyst volume and $V$, in cubic centimeters per second, is the volumetric flow rate at the temperature and pressure of the reactor.

EXAMPLE 1

A 0.513 g. sample of 40-100 mesh gamma-alumina (W200 basic activated alumina, I.C.N. Pharmaceuticals) was confined in a 316 stainless-steel tube of 1.8 cm. internal diameter and 9.0 cm. length. The alumina catalyst was treated with a flow of helium at 700° C. for about 10 hours. The BET surface area of the catalyst after this treatment was 120 m$^2$g$^{-1}$. A gas mixture containing acetophenone in helium with a total molar flow rate ($\bar{n}$) of 2.122 × 10$^{-4}$ mol/second, was passed through a preheater operating at a temperature of 80° C. and then into the tubular reactor. The gas stream leaving the reactor was passed through a liquid nitrogen trap to quench the products. At 600° C., 1084 Torr total pressure, 10.5 Torr partial pressure of acetophenone, a contact time of about 0.054 second and 90 minutes on stream, the selectivity for phenylacetylene formation (S) and total fractional conversion ($f$) were 0.65 and 0.78 respectively. Besides phenylacetylene and water, other products of the reaction were α-methylstyrene, cumene, styrene and benzene. Analysis of the products was made by gas chromatography.

EXAMPLE 2

A 50 g. sample of the gamma-alumina of Example 1 was wet with 20 cc. of a 2.67% aqueous solution of potassium hydroxide. This alkali-treated alumina was placed in a 200° C. oven and dried for 16 hours in a stream of nitrogen. The dried product was then charged to a quartz tube reactor unit 11.0 cm. in length and having an internal diameter of 4.0 cm., after which a mixture of oxygen and helium in a volume ratio of 2:3 was passed through the tube at a rate of 500 cc. per minute for 16 hours at 650° C. After this treatment, the alumina catalyst contained one mol percent of K$_2$O and had the same BET surface area as the catalyst in Example 1. The quartz reactor unit containing the catalyst was attached to a preheater composed of 50.0 cm. of quartz tubing having an outside diameter of 1.0 cm. coiled inside a jacket 15.0 cm. in length and having an internal diameter of 5.5 cm. Acetophenone then was dehydrated in this equipment following the conditions described in Example 1. The selectivity for phenylacetylene and total fractional conversion were 0.91 and 0.4, respectively. In addition to phenylacetylene and water, the product stream contained styrene, benzene, toluene and α-methylstyrene. The results obtained in this example, when compared to those of Example 1, demonstrate that, under the conditions used, the alumina containing one mol percent of K$_2$O was less active, as shown by the conversion values, but more selective for the dehydration of acetophenone to phenylacetylene than the untreated alumina. Apparently, the K$_2$O acts as an inhibitor, but inhibits the desired dehydration reaction to a lesser extent than the undesired side reactions resulting in formation of other products.

ditions of Example 3, and the data obtained both in Example 3 (Run No. 1) and in the present example (Runs Nos. 2, 3 and 4) are given in Table I.

Table I

| Run No. | Catalyst | Surface Area (BET) | Pore Diameter | Cut | Selectivity | Conversion (fractional) |
|---|---|---|---|---|---|---|
| 1 | 200 S gamma-alumina[1] plus 1.0 mol % $K_2O$ | 121 $m^2g^{-1}$ | 120 Å | 1 | 0.79 | 0.35 |
|   |   |   |   | 2 | 0.82 | 0.25 |
|   |   |   |   | 3 | 0.80 | 0.23 |
| 2 | 200 S gamma-alumina plus 0.1 mol % $K_2O$ | 120 $m^2g^{-1}$ | 100 Å | 1 | 0.61 | 0.44 |
|   |   |   |   | 2 | 0.68 | 0.33 |
|   |   |   |   | 3 | 0.78 | 0.22 |
| 3 | 200 S gamma-alumina | 118 $m^2g^{-1}$ | 100 Å | 1 | 0.67 | 0.43 |
|   |   |   |   | 2 | 0.72 | 0.36 |
|   |   |   |   | 3 | 0.79 | 0.26 |
| 4 | W-0801T tungsten trioxide-alumina[2] | 145 $m^2g^{-1}$ | 70 Å | 1 | 0.49 | 0.32 |
|   |   |   |   | 2 | 0.51 | 0.15 |
|   |   |   |   | 3 | 0.55 | 0.07 |

[1] Air Products and Chemicals, Inc.
[2] Harshaw Chemical Company

EXAMPLE 3

Following the procedure of Example 2, a sample of gamma-alumina (200 S, Air Products and Chemicals, Inc.) was treated with sufficient aqueous potassium hydroxide to produce a catalyst containing one mol percent of $K_2O$. The alkali-treated alumina was dried, and the 10–20 mesh product had a BET surface area of 121 $m^2g^{-1}$ and an average pore diameter of 120 Å. A 3.0 g. sample of the dried product was blended with 8.63 g. of quartz, and the resulting mixture was charged to a tubular quartz reactor unit, as in Example 2. The catalyst then was treated with a 2:1 mixture of nitrogen and oxygen by volume at 650° C. for 1 hour. A mixture of acetophenone in nitrogen with a total molar flow rate $\bar{n}$ = 4.4 × $10^{-5}$ mol/second was passed through the preheater of Example 2 at 600° C. and then into the tubular reactor. During the reaction, the product mixture from the reactor was quenched below −10° C. in a quencher, then passed through a hexadecane bubbler at room temperature and next into a dry-ice trap. Most of the high boiling components of the product mixture condensed in the quencher and the low boilers such as benzene and water were collected in the dry-ice trap. At 600° C., 10.5 Torr total pressure, 9.4 Torr partial pressure of acetophenone, a contact time of about 0.019 second and 10 minutes on stream in the reactor, the selectivity for phenylacetylene formation and the total fractional conversion were 0.79 and 0.35, respectively. The other products present besides phenylacetylene and water were α-methylstyrene, styrene and benzene. A total material balance for the acetophenone fed into the reactor and the products collected showed that more than 98% of the acetophenone could be accounted for. These results demonstrate that the dehydration of acetophenone can be accomplished with only a small amount of nitrogen diluent and, consequently, at a low total pressure.

EXAMPLE 4

During the reaction described in Example 3, two additional samples were collected and analyzed, one during the on-stream period from 10 minutes to 20 minutes and the other during the on-stream period from 20 minutes to 50 minutes. Thus, there was a first 10-minutes cut, a second 10-minutes cut and a third 30-minutes cut. This procedure was also followed in evaluating other alumina-containing catalysts using the con-

EXAMPLE 5

Run No. 2 of Example 4 was duplicated except to use temperatures of 550° C. and 500° C. and, in each instance, taking only cuts 1 and 2. At 550° C., in first cut exhibited a selectivity of 0.48 and a fractional conversion of 0.16. The corresponding values for the second cut were 0.56 and 0.18. At 500° C., the selectivity and fractional conversion values for the first cut were 0.25 and 0.07, respectively. The corresponding values for the second cut were 0.33 and 0.04 These data, when compared to that for Run No. 2 of Example 4, indicate that best results are obtained at a temperature of about 600° C.

EXAMPLE 6

The procedure of Example 3 was duplicated except to use different acetophenone partial pressures, taking only the first two cuts. At a partial pressure of 19 Torr, the first cut showed a selectivity of 0.7 and fractional conversion of 0.25. These values for the second cut were 0.74 and 0.21, respectively. At a partial pressure of 28 Torr, the selectivity and fractional conversion values for the first cut were 0.66 and 0.16, and the corresponding values for the second cut were 0.7 and 0.13. A run carried out at a partial pressure of 7 Torr gave a first cut exhibiting a selectivity of 0.86 and a fractional conversion of 0.396. These data and that obtained in Example 3 show the desirability of operating at a comparatively low acetophenone partial pressure.

EXAMPLE 7

The procedure of Example 3 was duplicated except to vary the contact time by changing the total molar flow rate of the acetophenone-nitrogen mixture. The second cuts were analyzed and compared to the second cut of Run No. 1 shown in Table I. At a contact time of 0.007 second, the selectivity was 0.86 and the fractional conversion was 0.14. At a contact time of 0.027 second, the corresponding values were 0.76 and 0.32, respectively. At a contact time of 0.041 second, the selectivity was 0.71 and the fractional conversion was 0.36. The results from these runs and from Run No. 1 shown in Table I indicate that the best balance between selectivity and fractional conversion occurs at a contact time of about 0.02 second.

EXAMPLE 8

One gram of the catalyst used in Run No. 3 of Example 4 was mixed with 11.1 g. of quartz, and the mixture was charged to a tubular quartz reactor unit, as in Example 2. Following generally the procedure of Example 3, m-diacetylbenzene was passed through the tubular reactor at 650° C., 10.0 Torr total pressure, 9.1 Torr partial pressure of the diacetylbenzene and a contact time of 0.0041 second for 10 minutes on stream. The selectivity for the formation of m-diethynylbenzene and the total fractional conversion were 0.66 and 0.16, respectively. The other products in the reaction mixture besides diethynylbenzene and water were m-ethynylacetophenone, acetophenone, methylacetophenone, m-isopropenylacetophenone and m-vinylacetophenone. Based on additional runs, it was found that product distribution depended considerably on the contact time. Comparable results were obtained in the conversion of p-diacetylbenzene to p-diethynylbenzene following the procedure of this example.

The dehydration process in accordance with this invention utilizes an alumina-containing catalyst. Preferred catalysts are alumina and alumina-silica compositions such as the synthetic and natural aluminum silicates, for example, kaolin and bauxite. Metallic oxides such as titanium dioxide, zirconium dioxide, thorium dioxide, chromic oxide, tungsten trioxide, ferric oxide, stannous oxide, nickel oxide and zinc oxide also may be used as dehydration catalysts in conjunction with the alumina catalyst. The most preferred catalyst is gamma-alumina. The catalyst may be in powder, lump or pellet form and preferably has a BET surface area of from about 10 to about 800 square meters per gram, more preferably from about 25 to about 160 square meters per gram. Representative pore diameters of the catalyst are in the range of from about 35 to about 1000 Å, preferably from about 100 to about 300 Å. Also, the catalyst preferably is pretreated with an alkali prior to use in the dehydration process, the amount of alkali being sufficient to cover part but not all of the catalyst surface. Satisfactory alkalies are the alkali metal hydroxides and carbonates, such as sodium hydroxide, potassium hydroxide, sodium carbonate and potassium carbonate. Moreover, the catalyst should be periodically regenerated to remove the organic material and carbon which are deposited on its surface during continued use in the process of this invention. Regeneration is accomplished by passing a stream of an oxygen-containing gas over the catalyst at an elevated temperature, such as 600° to 650° C., thereby burning off the carbonaceous deposits.

In the process of this invention, the temperature of the catalyst is critical to the successful operation of the process. It has been found that, at temperatures below about 500° C., the conversion of ketone to ethynylbenzene is too low to be of practical significance. On the other hand, at temperatures above 650° C., the yield of ethynylbenzene product decreases substantially and the life of the catalyst is relatively short, apparently due to the polymerization and carbonization of the ethynylbenzene products of the reaction. The preferred temperature range is from about 550° to about 600° C.

Moreover, a low partial pressure of the ketone and a short contact time of the ketone with the catalyst are important in that they insure rapid removal of the ethynylbenzene product from the reaction zone, thus minimizing loss of the ethynylbenzene product by further reactions such as polymerization and carbon formation. The partial pressure of the ketone should be in the range of from about 5 to about 30 millimeters of mercury. A partial pressure of about five millimeters of mercury is desirable to provide an adequate flow rate, and pressures above about 30 millimeters of mercury result in comparatively low fractional conversions. The preferable partial pressure of the ketone is in the range of from about 10 to about 20 millimeters of mercury.

The contact time should be within the range of from about 0.01 to about 0.05 second. A contact time of 0.01 second provides for significant conversion of the ketone to the ethynylbenzene product, and contact times much in excess of 0.05 second result in low yields of product and short catalyst life. The preferred contact times are in the range of from about 0.02 to about 0.04 second. It also is desirable in the process of this invention to effect rapid cooling of the gas stream leaving the reactor to prevent loss of the ethynylbenzene product by further reaction such as polymerization.

What I claim and desire to protect by Letters Patent is:

1. The process of preparing ethynylbenzenes which comprises contacting an acetylbenzene unsubstituted in the benzene ring except for the acetyl group(s) with an alumina-containing catalyst selected from the group consisting of alumina, a natural aluminum silicate or a synthetic aluminum silicate at a temperature in the range of from about 500° to about 650° C.

2. The process of claim 1 wherein the acetylbenzene is contacted with the catalyst for a period of time of from about 0.01 to about 0.05 second and at an acetylbenzene partial pressure of from about 5 to about 30 mm. of mercury.

3. The process of claim 1 wherein the alumina-containing catalyst is gamma-alumina.

4. The process of claim 3 wherein the gamma-alumina catalyst has a BET surface area of from about 10 to about 800 square meters per gram and a pore diameter of from about 35 to about 1000 Å.

5. The process of claim 4 wherein the surface of the catalyst has been treated with an alkali metal hydroxide or carbonate.

6. The process of claim 1 wherein the acetylbenzene is acetophenone and the ethynylbenzene product is phenylacetylene.

7. The process of claim 1 wherein the acetylbenzene is a diacetylbenzene and the ethynylbenzene product is a diethynylbenzene.

8. The process of claim 7 wherein the diacetylbenzene is m-diacetylbenzene and the diethynylbenzene is m-diethynylbenzene.

9. The process of claim 7 wherein the diacetylbenzene is p-diacetylbenzene and the diethynylbenzene is p-diethynylbenzene.

* * * * *

UNITED STATES PATENT AND TRADEMARK OFFICE
CERTIFICATE OF CORRECTION

PATENT NO. : 4,120,909
DATED : October 17, 1978
INVENTOR(S) : AMIRNAZMI, ALI

It is certified that error appears in the above-identified patent and that said Letters Patent are hereby corrected as shown below:

In Col. 2 at line 1;

"$S = f/f$"   should read   -- $S = f'/f$ --.

In Col. 2 at line 3;

"where f"   should read   --where $f'$--.

Signed and Sealed this

Twenty-third Day of January 1979

[SEAL]

Attest:

RUTH C. MASON
Attesting Officer

DONALD W. BANNER
Commissioner of Patents and Trademarks